United States Patent
Reicher et al.

(10) Patent No.: US 8,939,153 B1
(45) Date of Patent: Jan. 27, 2015

(54) TRANSPONDER STRINGS

(71) Applicant: Health Beacons, Inc., The Woodlands, TX (US)

(72) Inventors: Murray A. Reicher, Rancho Santa Fe, CA (US); Robert Petcavich, The Woodlands, TX (US)

(73) Assignee: Health Beacons, Inc., The Woodlands, TX (US)

( * ) Notice: Subject to any disclaimer, the term of this patent is extended or adjusted under 35 U.S.C. 154(b) by 0 days.

(21) Appl. No.: 14/209,638

(22) Filed: Mar. 13, 2014

Related U.S. Application Data (60) Provisional application No. 61/793,111, filed on Mar. 15, 2013.

(51) Int. Cl.
*A61B 19/00* (2006.01)
*A61B 5/00* (2006.01)
*A61B 5/06* (2006.01)

(52) U.S. Cl.
CPC ............ *A61B 5/0031* (2013.01); *A61B 5/065* (2013.01); *A61B 5/6848* (2013.01)
USPC ........... 128/897; 600/381; 600/374; 600/378; 600/393; 600/424; 600/373; 128/898; 128/899

(58) Field of Classification Search
CPC ..... A61B 5/042; A61B 5/0422; A61B 5/0492
USPC ................. 600/373, 381, 374, 378, 393, 424; 606/129; 128/897–899
See application file for complete search history.

(56) References Cited

U.S. PATENT DOCUMENTS

| | | | |
|---|---|---|---|
| 4,592,356 A | 6/1986 | Gutierrez | |
| 4,809,713 A | 3/1989 | Grayzel | |
| 5,011,473 A | 4/1991 | Gatturna | |
| 5,059,197 A | 10/1991 | Urie et al. | |
| 5,099,845 A | 3/1992 | Besz et al. | |
| 5,127,916 A * | 7/1992 | Spencer et al. | 606/185 |
| 5,158,084 A | 10/1992 | Ghiatas | |
| 5,197,482 A | 3/1993 | Rank | |
| 5,221,269 A | 6/1993 | Miller et al. | |
| 5,325,873 A | 7/1994 | Hirschi et al. | |
| 5,409,004 A | 4/1995 | Sloan | |
| 5,709,697 A | 1/1998 | Ratcliff et al. | |

(Continued)

FOREIGN PATENT DOCUMENTS

EP 0 967 927 B1 4/2003
WO WO 98/30166 7/1998

(Continued)

*Primary Examiner* — Christine H Matthews
*Assistant Examiner* — Sunita Reddy
(74) *Attorney, Agent, or Firm* — Knobbe, Martens, Olson & Bear, LLP (57) ABSTRACT

A transponder string comprising multiple transponders is configured for injection into human tissue. In one embodiment, the transponders are sized to move through a needle for injection into the human tissue. Positions of the transponders with reference to one another may be maintained by coupling the transponders via a filament, adhesive backed substrate, shrink tubing, and/or any other suitable substrate. The transponders are configured to transmit data to a mobile computing device, e.g., a wand, smart phone or wireless tablet positioned outside the human tissue such that positions of the transponders are determinable, e.g., during an excision surgery.

13 Claims, 5 Drawing Sheets

(56) References Cited

U.S. PATENT DOCUMENTS

| | | | |
|---|---|---|---|
| 5,952,935 | A | 9/1999 | Mejia et al. |
| 5,989,265 | A | 11/1999 | Bouquet De La Joliniere et al. |
| 6,026,818 | A | 2/2000 | Blair et al. |
| 6,161,034 | A | 12/2000 | Burbank et al. |
| 6,173,715 | B1 | 1/2001 | Sinanan et al. |
| 6,184,777 | B1 | 2/2001 | Mejia |
| 6,239,724 | B1 | 5/2001 | Doron et al. |
| 6,261,247 | B1 | 7/2001 | Ishikawa et al. |
| 6,363,940 | B1 | 4/2002 | Krag |
| 6,398,710 | B1 * | 6/2002 | Ishikawa et al. ............... 600/3 |
| 6,427,081 | B1 | 7/2002 | Burbank et al. |
| 6,496,717 | B2 | 12/2002 | Cox et al. |
| 6,567,689 | B2 | 5/2003 | Burbank et al. |
| 6,995,729 | B2 | 2/2006 | Govari et al. |
| 7,026,941 | B1 | 4/2006 | Anderson |
| 2001/0020148 | A1 * | 9/2001 | Sasse et al. .................... 604/65 |
| 2002/0046756 | A1 | 4/2002 | Laizzo et al. |
| 2002/0107445 | A1 * | 8/2002 | Govari ........................ 600/437 |
| 2003/0004411 | A1 | 1/2003 | Govari et al. |
| 2003/0018246 | A1 | 1/2003 | Govari et al. |
| 2003/0023161 | A1 | 1/2003 | Govari et al. |
| 2003/0120150 | A1 * | 6/2003 | Govari ........................ 600/424 |
| 2004/0236193 | A1 | 11/2004 | Sharf |
| 2005/0033108 | A1 | 2/2005 | Sawyer |
| 2005/0165305 | A1 | 7/2005 | Foerster et al. |
| 2006/0084865 | A1 | 4/2006 | Burbank et al. |
| 2006/0155190 | A1 | 7/2006 | Burbank et al. |
| 2006/0241396 | A1 | 10/2006 | Fabian et al. |
| 2006/0258933 | A1 | 11/2006 | Ellis et al. |
| 2007/0016009 | A1 | 1/2007 | Lakin et al. |
| 2007/0249901 | A1 | 10/2007 | Ohline et al. |
| 2008/0086046 | A1 | 4/2008 | Petcavich et al. |
| 2009/0131825 | A1 | 5/2009 | Burbank et al. |

FOREIGN PATENT DOCUMENTS

| | | |
|---|---|---|
| WO | WO 2007/087447 | 8/2007 |
| WO | WO 2007/117478 | 10/2007 |

* cited by examiner

TRANSPONDER STRINGS

CROSS-REFERENCE TO RELATED APPLICATIONS

This application claims priority benefit under 35 U.S.C. §119(e) of U.S. Provisional Application No. 61/793,111, filed on Mar. 15, 2013, which is hereby incorporated by reference in its entirety.

BACKGROUND OF THE INVENTION

A transponder, as used herein, refers to any number of devices that are configured to receive a charge from an external device and to transmit a wireless signal in response. For example, one type of transponder is an RFID tag that is powered by a wand (or reader) that emits radiation, wherein the RFID tag uses power in the radiation in order to transmit a signal that may be read by the wand. Other transponders may be powered by other energy sources to similarly provide enough power to the transponder to transmit a signal that is readable by a wand (or other reading device). Another example transponder, referred to as an embedded passive integrated transponder, is discussed in co-pending application Ser. No. 12/371,048, filed Feb. 13, 2009, entitled "Method and apparatus for locating passive integrated transponder tags," which is hereby incorporated by reference in its entirety and for all purposes.

SUMMARY OF THE INVENTION

The systems, methods, and devices described herein each have several aspects, no single one of which is solely responsible for its desirable attributes. Without limiting the scope of this disclosure, several non-limiting features will now be discussed briefly.

In one embodiment, a transponder array comprising a plurality of transponders configured for injection into human tissue, each of the plurality of transponders including one or more electrical components configured to transmit data to a mobile computing device positioned outside the human tissue such that positions of the transponders are determinable based on the transmitted data, wherein the plurality of transponders are sized to move through a needle for injection into the human tissue and are each coupled to an attachment mechanism such that the transponders are positioned apart from one another in a substantially linear pattern. In one embodiment, the attachment mechanism comprises filament. In one embodiment, the attachment mechanism comprises a substrate such that the transponders are positioned apart from one another in the substantially linear pattern. In one embodiment, the substrate comprises one or more layers of tape or adhesive. In one embodiment, individual transponders of the plurality of transponders are configured to store information that uniquely identifies the individual transponder. In one embodiment, the information stored by the transponders identifies an area of placement of the respective transponder within the human tissue. In one embodiment, the information stored by the transponders identifies a location of the respective transponder with reference to other transponders in the transponder string. In one embodiment, each transponder has dimensions of no more than 1 millimeter in any dimension. In one embodiment, each transponder is configured to be activated by visible light radiation such that the transponder is powered to transmit the data to the mobile computing device. In one embodiment, the mobile computing device comprises a wand.

In another embodiment, a method of locating an area of interest in human tissue having a string of transponders positioned therein such that one end of the string of transponders is near a surface of the human tissue and the other end of the string of transponders is near the object of interest deeper in the human tissue comprises, with a reading device configured to provide energy sufficient to power the transponders when placed within a particular distance of a transponder such that the powered transponder transmits wireless data including an identifier of the powered transponder that is different than identifiers of at least some of the other transponders in the string of transponders, powering a first of the transponders, receiving a first identifier from the first transponder, and determining a location of the first transponder with reference to other transponders in the string of transponders based on at least the first identifier. In one embodiment, the string of transponders are coupled in series by a filament or an adhesive backed substrate and the method further comprises following the filament or adhesive backed substrate into the tissue in order to locate other transponders of the string of transponders. In one embodiment, the string of transponders are not coupled to one another and the method further comprises determining an approximate location of another transponder and/or the area of interest based at least on the determined location of the first transponder.

In another embodiment, a method of inserting a string of transponders into tissue comprises loading a needle with a string of transponders coupled in a predetermined pattern by a filament or an adhesive backed substrate and having an anchoring mechanism at a proximal end, inserting the needle into tissue until a proximal end of the needle is at an area of interest within the tissue, moving the string of transponders towards the proximal end of the needle so that the anchoring mechanism exits the needle, and removing the needle such that the anchoring mechanism remains attached to the area of interest and the string of transponders are positioned at varying positions between a surface of the tissue and the area of interest. In one embodiment, the anchoring mechanism comprises one or more hooks.

DETAILED DESCRIPTION OF THE PREFERRED EMBODIMENT

Transponders may vary greatly in size. For example, a light-powered transponder may be many times smaller than a standard RFID tag. Thus, use of smaller light-powered transponders may be preferred in many applications. The systems and methods describes herein may be applied to any type of transponder of any size, such as smaller transponders that are developed in the future.

Transponders may include antennas that transmit information for reading by a wand (or other device, such as a smart phone or wireless tablet), such as through a magnetic field created near the transponder as a result of modulated current in the antenna loop. Transponders may communicate with readers in any other manner. A transponder may have a unique ID and/or other information that may be transmitted. One example of a light power transmitter is the p-Chip manufactured by PHARMASEQ. Such transponders are typically used to track inventory, tools, etc.

Described herein are systems and methods for use of transponder strings, where the term "transponder string" refers generally to a plurality of transponders that are connected and/or placed in a spatial pattern with reference to one another. Systems and methods for placement and use of transponders strings in mammalian tissue are discussed herein. For purposes of discussion, the transponder strings may be discussed herein with reference to human tissue, but the same and/or similar uses may be realized with other mammalian tissue (or non-mammalian tissue, or even a non-organic substrate). A transponder string may advantageously allow placement of a small transponder near a surface of human tissue so that it may be detected with a small amount of radiation (e.g. by light radiation), while allowing a surgeon (or other) to follow the string of transponders in order to reach an object or area of interest within the tissue.

Figure 1:
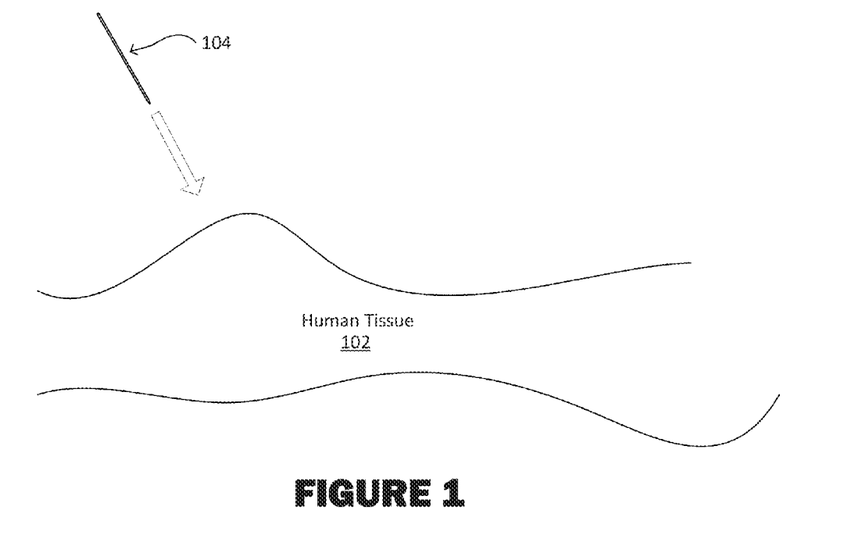
FIG. 1 illustrates an example human tissue and a needle that may be loaded with a transponder string for placement in the human tissue, according to one embodiment.

FIG. 1 illustrates an example human tissue 102 and a needle 104 that may be loaded with a transponder string for placement in the human tissue. Depending on embodiment, different types of needles, or other tools, may be used to insert transponder strings into tissue.

Figure 2:
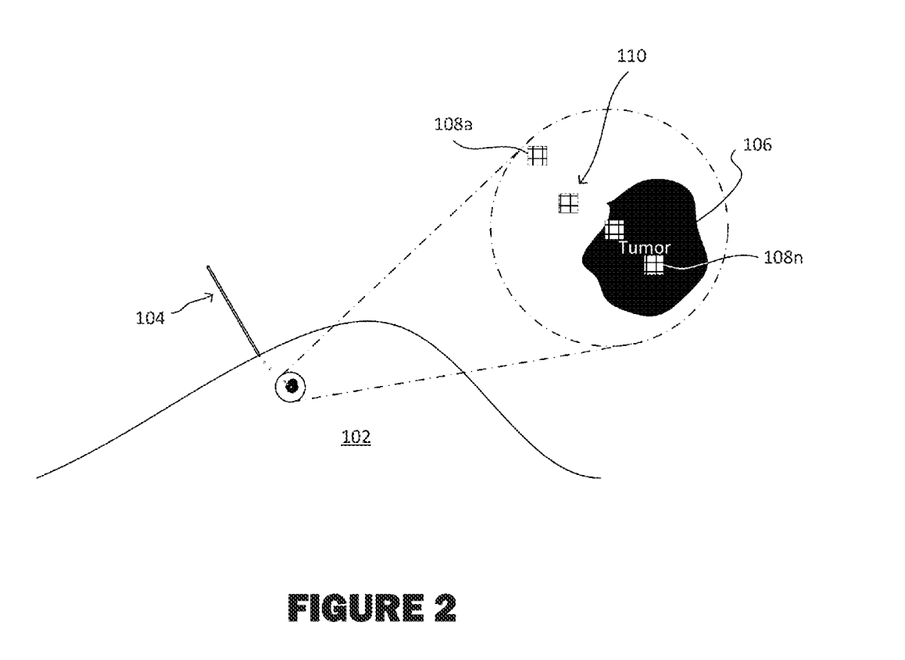
FIG. 2 illustrates a needle being withdrawn from tissue in order to leave a transponder string within the tissue, according to one embodiment.

FIG. 2 illustrates needle 104 being withdrawn from the tissue 102 in order to leave a transponder string 110 within the tissue. In the example of FIG. 2, the transponder string is placed with one end located within a tumor 106, and the other end of the transponder string placed near a surface of the tissue 102. With the transponder string 110 placed in this manner, a surgeon may identify the first transponder 108a near a surface of the tissue 102 using a radiation source that may not have sufficient power to reach (or to provide adequate power to) one or more deeper transponders, such as transponder 108n that is placed in or near the tumor 106. Accordingly, once the surgeon (or other) has located one transponder in the transponder string 110, the remaining transponders can be found by following the transponder string into the tissue 102. Thus, a transponder string that is located entirely below the skin surface may be located and followed to an area of interest.

In the embodiment of FIG. 2, the transponder string is illustrated without a physical attachment mechanism between the individual transponders 108. In one embodiment, the transponders may be placed in the human tissue without physical attachment between the transponders. In this embodiment, the unique IDs of individual transponders may be usable to determine a relative position of particular transponders within the transponder string.

In other embodiments, the transponder string may be physically coupled with an attachment mechanism, such as a filament, string, wire, tape, and/or any other suitable attachment material. While only four transponders are illustrated in FIG. 2, any number of transponders may be arranged in a transponder string. For example, a transponder string comprising 10, 20, 50, or 100 transponders may be used to mark a path and/or an area of interest for a surgeon and/or other interested party. Thus, the transponder that is positioned on the tumor in FIG. 2 is denoted as 108n to indicate that any number of transponders may be included between transponder 108a and 108n.

Depending on the embodiment, the transponder string may end on the area of interest (e.g., on the tumor 106 of FIG. 2) and/or may surround (partially or fully) an area of interest (e.g., transponders may surround a tumor to indicate borders of a planned biopsy).

Figure 3:
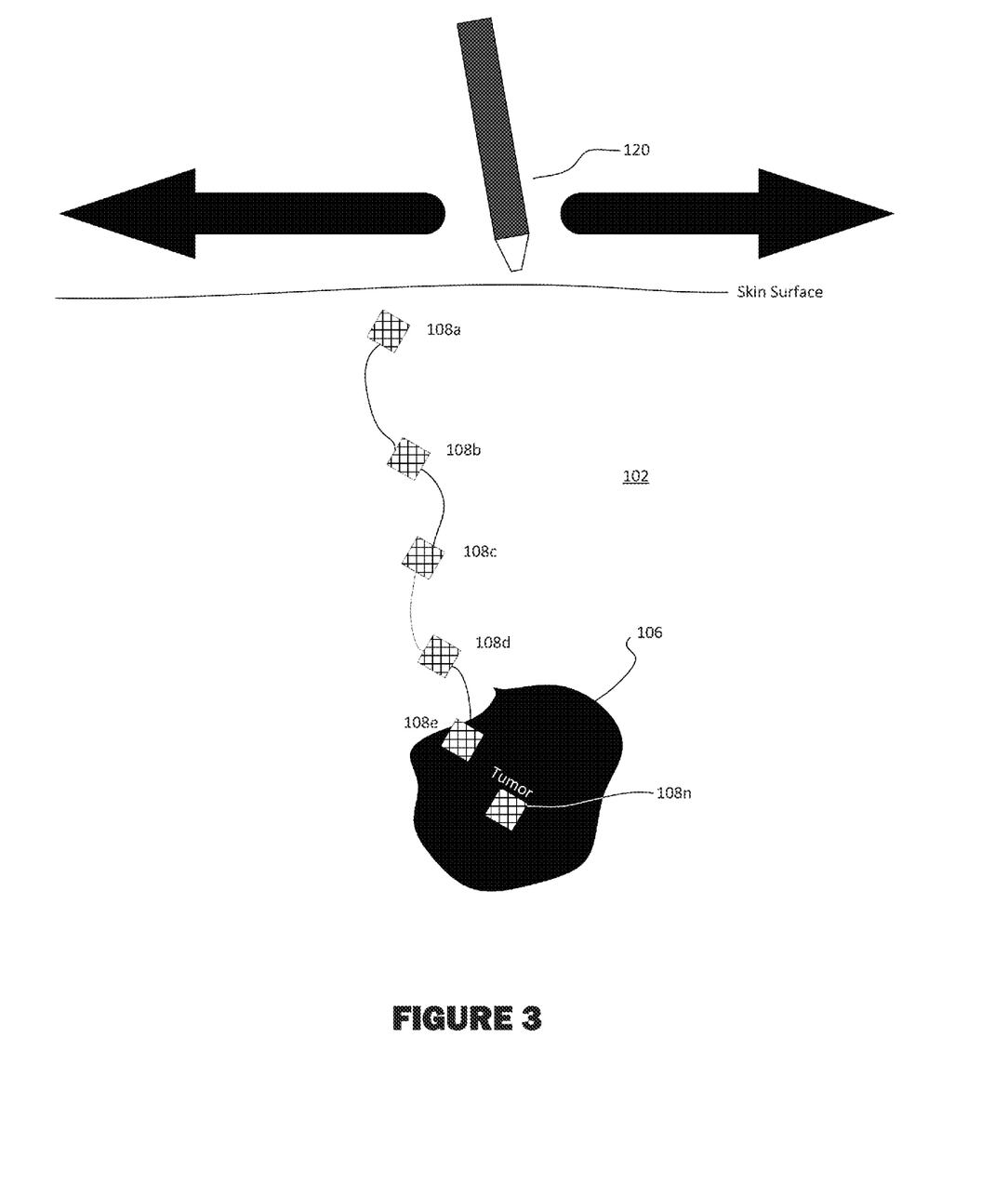
FIG. 3 illustrates a transponder string positioned in tissue, wherein a reader (e.g., a wand) is positioned to identify one or more of the transponders, according to one embodiment.

FIG. 3 illustrates a transponder string, including any number of transponders 108a to 108n, positioned in tissue, wherein a reader 120 (or wand 120, smart phone, wireless tablet, or other reading device) is positioned to identify one or more of the transponders. As noted above, the reader 120 may include both a radiation source and a receiver, such that the reader 120 may provide power to the transponders and may also receive data transmissions returned from the activated transponders. In the example of FIG. 3, the reader 120 may be moved back and forth along the skin surface in an area where the transponder string is believed to begin, until a feedback signal is received from one or more of the transponders. For example, the reader 120 may have sufficient power to power multiple transponders that are nearest the skin surface (e.g., transponders 108a and 108b), or may only have sufficient power to power a transponder that is very near the skin surface, such as transponder 108a, when the transponder is substantially above the transponder on the skin surface. Once a transponder is identified, data returned from the transponder may be used in determining how/where incisions should be initiated in order to traverse the transponder string towards an area of interest.

Figure 4:
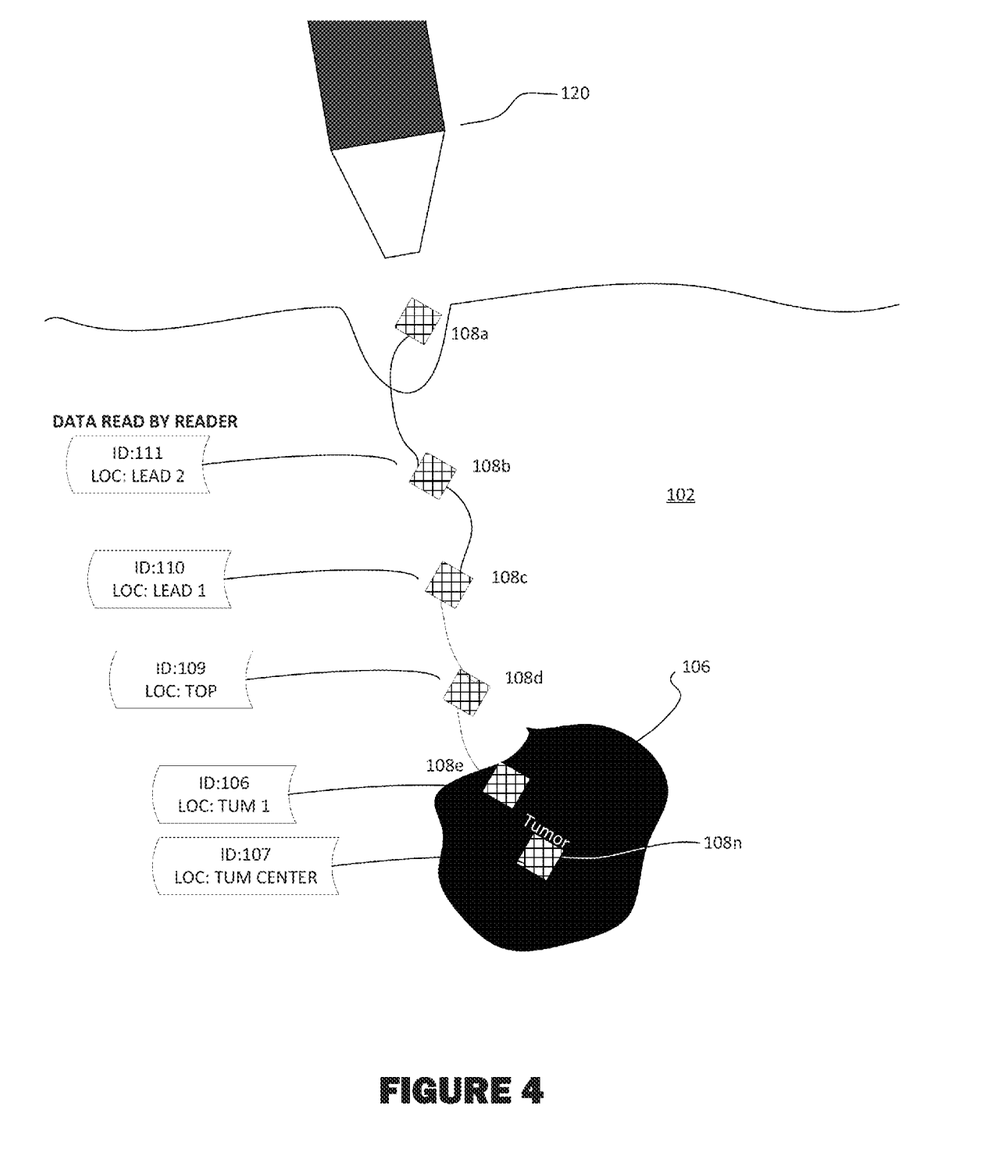
FIG. 4 illustrates the transponder string of FIG. 3, now with example data that may be stored on individual transponders indicated to the left of respective transponders, according to one embodiment.

FIG. 3 illustrates exposure of the first transponder 108a, such as after an initial incision is made on the tissue 102 above an area where the reader 120 identified the transponder 108a. In the embodiment of FIG. 4, example data that may be stored on individual transponders is indicated on the left of the figure. For example, the transponder 100b may include a unique ID ("111") and also a location identifier ("LEAD 2"). This may indicate that the transponder 108b is the second transponder away from a transponder that marks a top of the area of interest (e.g., the tumor 106 in this example). Similarly, the transponder 108c may include a unique ID ("110") and also a location identifier ("LEAD 1"), which may indicate that the transponder 108c is the first transponder next to a transponder that marks a top of the area of interest. The other location identifiers in this example indicate, for example, a top of the tumor ("TOP" identifier in transponder 108d), an area within the tumor ("TUM 1 identifier in transponder 108e), and a tumor center ("TUM CENTER" identifier in transponder 108n). Thus, the surgeon can determine a relative location of any one transponder based on the location identifier returned from the transponder. In other embodiments, the nomenclature and/or categorizations of areas of interest that are marked by particular transponders various. For example, in one embodiment the transponders may be programmed to include custom nomenclature.

Additionally, in some embodiments the location identifiers are not stored on the transponders themselves, but rather are associated with the transponder ID in a data structure that is accessible to the user. Thus, the surgeon may associate transponder ID 111 with location identifier LEAD 2 by accessing a data structure that stores the information, such as a data structure that is generated when the transponder string is initially placed in the tissue. In one embodiment, the data structure is accessible to a computing system that is in communication with the reader 120 (e.g., either via a wired or a wireless communication channel), such that when a transponder ID is read, the computing system automatically provides a corresponding location identifier from a data structure. Unique transponder IDs and/or identifiers enable one to know the relative position of each marker, the order along the string, and/or where the transponder is intended to be relative to the target (e.g., is this transponder at the center, edge, or other margin of the target). In some embodiments, the filament may also be placed to mark a location, or locations, of a lesion, such as the margins of a lesion and/or edges of the lesion.

Figure 5:
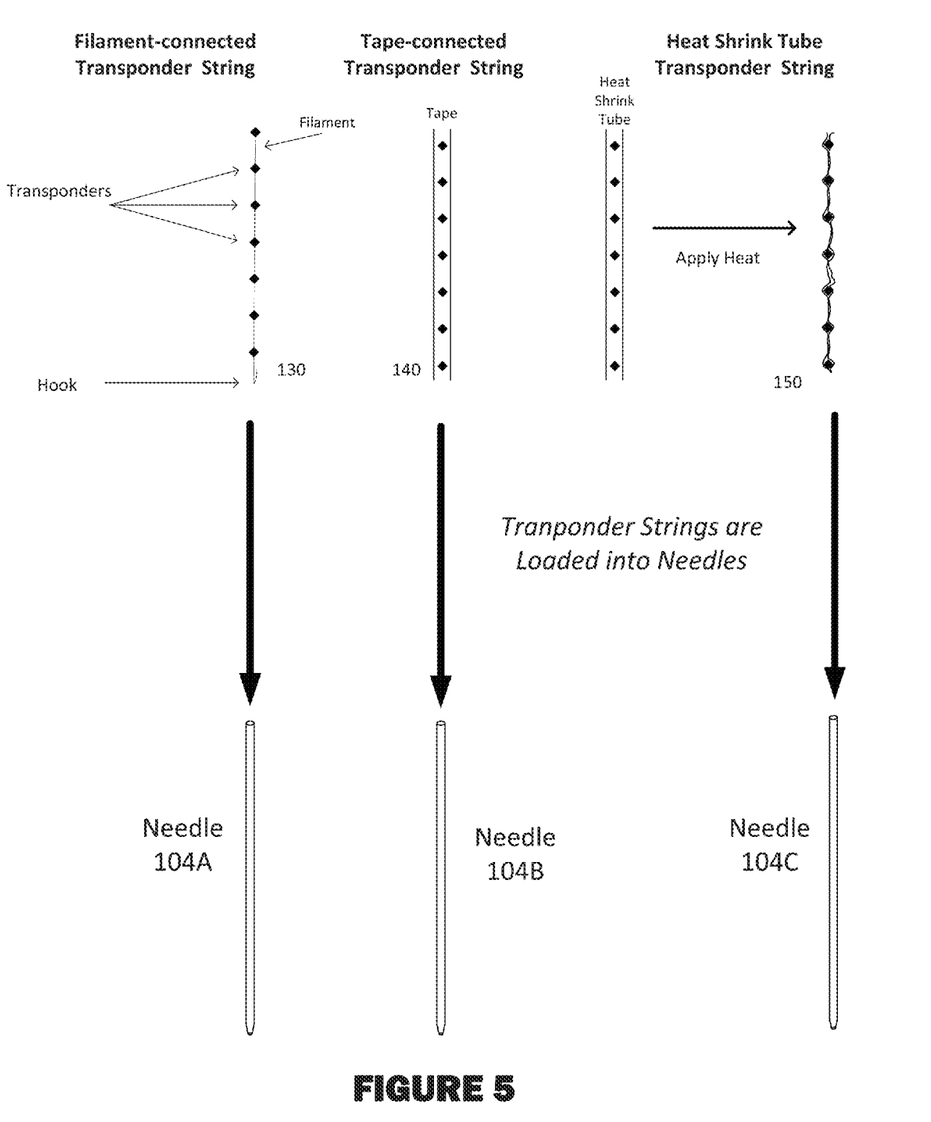
FIG. 5 illustrates three different types of transponder strings that may be loaded into the needles and inserted into tissue, according to one embodiment.

FIG. 5 illustrates example needles 104A, 104B, and 104C (which may be identical sizes or may have different inner diameters, outer diameters, lengths, etc.) and three different types of transponder strings that may be loaded into the respective needles 104 and inserted into tissue. In particular, FIG. 5 illustrates a filament-connected transponder string 130, a tape-connected transponder string 140, and a heat shrink tube transponder string 150. Such filaments could range in length from one cm to many cm, and might be a fraction of a millimeter in diameter up to 5 or more millimeters.

The transponders of the filament-connected transponder string 130 are coupled together in the series configuration via a filament, such as a thread, string, wire, monofilament, polysulfone, polycaprolactone, cellulosics, and/or other suitable material. The filament may be composed of any material, such as absorbable materials including polyglycolic acid, polylactic acid, Monocryl and polydioxanone, and/or non-absorbable materials such as nylon, polyester, PVDF and polypropylene. In one embodiment, an absorbable suture may be used in patients wherein a non-absorbable suture may cause an adverse reaction when left in the patient's body.

In one embodiment, the filament is a single structure, and the individual transponders are adhered to the filament at periodic locations along the filament. In another embodiment, the filament may include multiple segments that are each attached on their ends to different transponders to create a filament-connected transponder string 130 such as is illustrated in FIG. 5. In one embodiment, an adhesive is used to attach the transponders to the filament. In other embodiments, the filament is attached in other manners, such as by looping the filament through an aperture in the individual transponders and/or otherwise tying the filament to the individual transponders. In the example of transponder string 130, a hook is attached at an end of the transponder string, and is configured to anchor the transponder string at a desired location within the tissue. Depending on the embodiment, other anchoring mechanisms may be used in order to anchor the transponder string (or no anchoring mechanism may be used in certain embodiments, and/or multiple anchoring mechanisms (e.g., multiple hooks) may be used at the end of a transponder string and/or at other locations along the transponder string.

The transponders of the tape-connected transponder string 140 are held in a periodic distribution by one or more layers of an adhesive tape to which the transponders are attached. For example, the transponders may be placed on a first layer of adhesive tape (or other type of adhesive material) in a periodic distribution, and the adhesive tape may then be folded around the transponders such that the adhesive surface is not outwardly exposed. Alternatively, another layer of adhesive tape (or possibly non-adhesive material) may be placed on top of the first layer of adhesive tape after the transponders have been placed thereon. Similar to the transponder string 130, an anchoring mechanism may be included on an end of the transponder string 140, such as a hook or any other anchoring mechanism.

In another embodiment, transponders may be placed in heat shrinkable tubing. For example, transponders may be placed along a filament, catheter or implantable tube which is then coaxially surrounded by a heat-shrinkable material. By heat-shrinking the surrounding sleeve, the transponders could thus be bound to the underlying filament, catheter or tube. Thus, the heat shrinkable tubing may be used alone to secure transponder in position with reference to one another, or in conjunction with another of the transponder connection mediums discussed above. Once the heat shrinkable tube has been shrunk around the transponders, the tube can be loaded into a needle for positioning in the patient (as discussed above) and/or positioning in the patient in any other manner. In another embodiment, transponders may be placed in a tube at a predetermined distance from one another and then the tubing is heated in order to shrink around the transponders and hold them in position relative to one another. In another embodiment, transponders are placed on another substrate, such as a filament or an Endotracheal tube, for example, and then inserted in the heat shrinkable tubing prior to heating/shrinking the tubing.

In other embodiments, transponder strings may be adhered to any other structure and/or placed in a periodic distribution pattern by any other means. The distribution pattern may be determined in various manners. For example, different gaps between transponders may be used for different applications. Thus, for one surgical procedure the transponders may be positioned a first distance X apart (e.g., X=2 mm, 4 mm, 6 mm, 8 mm, 10 mm, etc.), while for another surgical procedure the transponders may be positioned a distance X/Y or X*Y apart (e.g., some fraction of or multiple of the first distance). In some embodiments, the gaps between transponders are not uniform. For example, gaps between transponders may increase along the length of the transponder string, such that the initially inserted transponders (e.g., closest to a lesion) are closer together than the later inserted transponders (e.g., furthest from the lesion). In some embodiments, transponders strings may be manufactured in particular lengths and transponder configurations for particular medical uses. For example, a breast lesion transponder string may be manufactured at a length of 6-8 cm with transponders on the initial 2 cm grouped very tightly (e.g., a very small uniform gap between the transponders) with a much smaller number of transponders in the remaining 2 cm or more cms (e.g., gaps increase as move further from the initial 2 cm portion or an increased gap is uniformly used in that 2 cm section). Other configurations of transponder strings that are customized for specific uses may be manufactured using the various methods discussed herein.

In one embodiment, a transponder string and a delivery device, such as a needle, may be packaged together for easy use by the doctor, surgeon, etc. For example, a needle may be preloaded with a transponder string (possibly one of a particular length, material, and/or with a certain spacing and quantity of transponders for a particular use) and packaged for use, such as in a common shrink-wrapped packaging. Thus, in one embodiment a kit comprises a transponder string and a delivery device.

Figure 6:
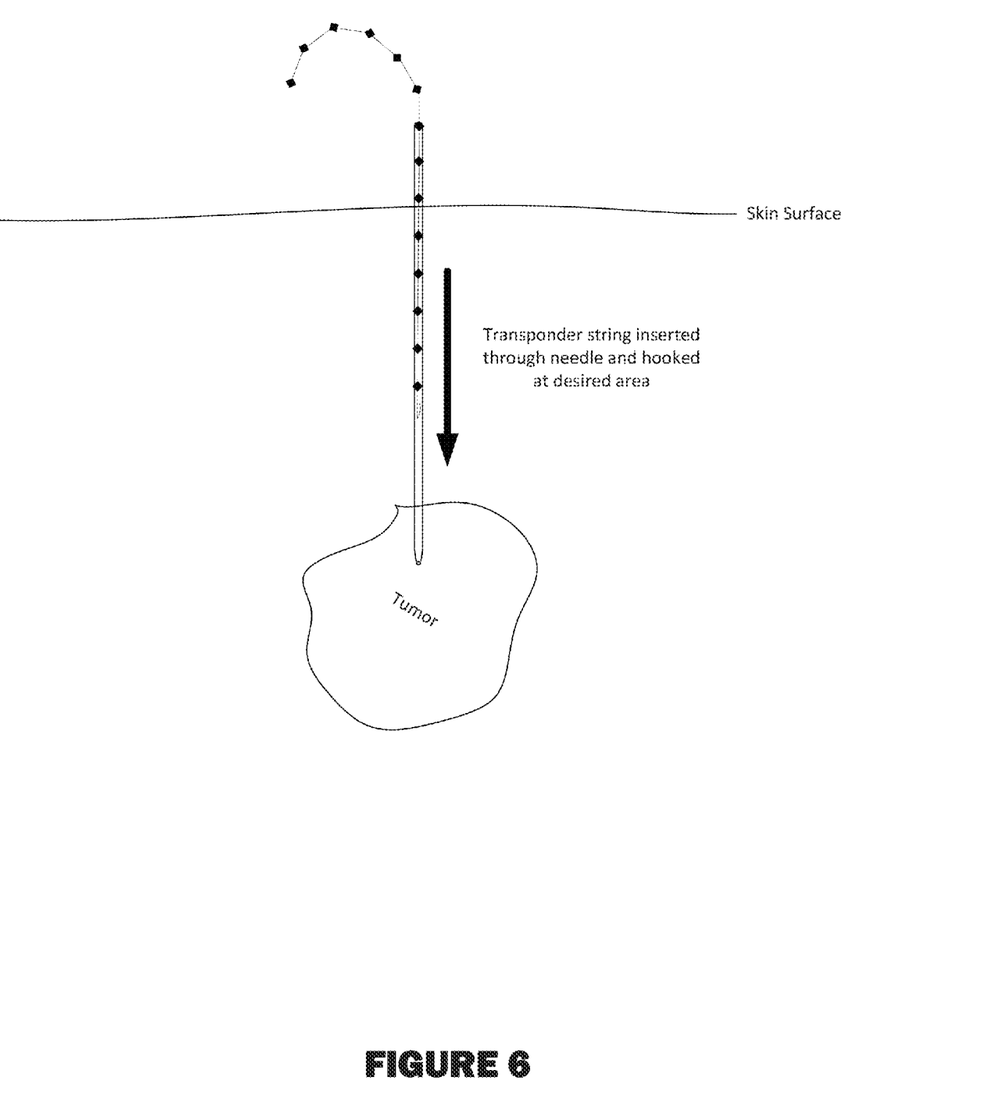
FIG. 6 illustrates a needle inserted into an area of interest (e.g., tumor) and a transponder string being loaded into the needle, according to one embodiment.

In the embodiment of FIG. 6, the transponder string 130 or 140 may be loaded into the needle 104 and inserted into the tissue via a lower end of the needle. FIG. 6 illustrates, for example, a needle inserted into an area of interest (e.g., tumor) and a transponder string being loaded into the needle. The transponder string may be pushed out of the needle into the tumor and then the needle may be removed in order to anchor the transponder string (e.g., using the hook) on the tumor, with the spaced transponders extending from the tumor to the skin surface. Depending on the embodiment, the transponder string may be pre-sized so that the last transponder is positioned just below the skin surface. In other embodiments, the transponder string may be cut at the appropriate position to leave one or more transponders just below the skin surface.

SUMMARY

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A transponder array comprising:
a plurality of transponders each providing equivalent functionality and configured for injection into human tissue, each of the plurality of transponders including one or more electrical components configured to transmit data indicating unique identifiers of transponders to a handheld mobile computing device such that positions of the transponders within the plurality of transponders are determinable based on the data transmitted to the handheld mobile computing device, wherein first information stored by a first transponder identifies a location of the first transponder with reference to other transponders in the transponder array; and
a biologically absorbable suture connected to each of the plurality of transponders and defining a predetermined distance between adjacent pairs of the plurality of transponders,
wherein the plurality of transponders and the biologically absorbable suture are sized to move through a needle for injection into the human tissue.

2. The transponder array of claim 1, wherein the predetermined distance is substantially the same between each adjacent pair of transponders.

3. The transponder array of claim 1, wherein the first information stored by the first transponder identifies an area of placement of the first transponder within the human tissue.

4. The transponder array of claim 1, wherein each transponder has dimensions of no more than 1 millimeter in any dimension.

5. The transponder array of claim 1, wherein each transponder is configured to be activated by visible light radiation such that each transponder is powered to transmit the data to the handheld mobile computing device.

6. The transponder array of claim 1, wherein the handheld mobile computing device comprises a wand.

7. The transponder array of claim 1, wherein the biologically absorbable suture secures the transponders positioned apart from one another in a substantially constant pattern.

8. The transponder array of claim 1, wherein the biologically absorbable suture comprises polylactic acid.

9. A method of locating an area of interest in a human tissue having a string of transponders positioned therein the method comprising:
moving a reading device over the area of interest in the human tissue having the string of transponders embedded therein, with one end of the string of transponders adapted to be placed near a surface of the human tissue and the other end of the string of transponders adapted to be placed near an object of interest deeper in the human tissue,
wherein each of the transponders provides equivalent functionality;
wherein the reading device provides energy sufficient to power the transponders when placed within a particular distance of respective transponders such that the powered transponders transmit wireless data including an identifier of respective powered transponders that are different than identifiers of at least some of other transponders in the string of transponders;
receiving, via the reading device, dynamic proximity indications regarding proximity of the reading device to one or more of the transponders in the human tissue as the reading device is moved with reference to the string of transponders;
identifying, based on the dynamic proximity indications, a first location of a first transponder of the string of transponders adapted to be positioned near the surface of the human tissue;
identifying a portion of the string attached to the first transponder and adapted to extend deeper into the human tissue; and
following the portion of the string in order to locate a second transponder of the string of transponders also attached to the first portion of the string.

10. The method of claim 9, wherein the string of transponders are coupled in series by a filament or an adhesive backed substrate, the method further comprising:
identifying a second portion of the string attached to the second transponder and adapted to extend deeper into the human tissue; and
following the second portion of the string in order to locate a third transponder of the string of transponders also attached to the second portion of the string.

11. A method of inserting a string of transponders into tissue, the method comprising:
loading a needle with the string of transponders coupled in a predetermined pattern by the string and having an anchoring mechanism at a proximal end, each of the transponders configured to transmit data to a mobile computing device indicating a unique identifier of the transponder indicative of a transponder position with reference to other transponders in the string of transponders;

inserting the needle into tissue until a proximal end of the needle is at an area of interest within the tissue;

moving the string of transponders towards the proximal end of the needle so that the anchoring mechanism exits the needle; and removing the needle such that the anchoring mechanism remains attached to the area of interest and the string of transponders are positioned at varying tissue depths between a surface of the tissue and the area of interest.

12. The method of claim 11, wherein the anchoring mechanism comprises one or more hooks.

13. A method of manufacturing a transponder array, the method comprising:

arranging a plurality of transponders to have a predetermined spacing between adjacent transponders;

placing a heat shrinkable material around the plurality of transponders; and heating the heat shrinkable material to secure the plurality of transponders at the predetermined spacing via compacted heat shrinkable material and forming a transponder array configured for injection into mammalian tissue through a needle, wherein each of the plurality of transponders includes one or more electrical components configured to transmit data to a mobile computing device uniquely identifying the transponders.

* * * * *